(12) United States Patent
Hochi et al.

(10) Patent No.: US 10,531,988 B2
(45) Date of Patent: Jan. 14, 2020

(54) LAMINATED FILM AND MEDICAL SHEET

(71) Applicants: Toray Industries, Inc., Tokyo (JP); NANOTHETA CO, LTD., Tokyo (JP)

(72) Inventors: Motonori Hochi, Otsu (JP); Yuki Sekido, Otsu (JP); Akihiro Saito, Otsu (JP); Shinji Takeoka, Tokyo (JP); Shinya Ohtsubo, Chofu (JP); Akinari Hinoki, Tokorozawa (JP); Manabu Kinoshita, Tokorozawa (JP)

(73) Assignees: Toray Industries, Inc., Tokyo (JP); NANOTHETA CO, LTD., Tokyo (JP)

( * ) Notice: Subject to any disclaimer, the term of this patent is extended or adjusted under 35 U.S.C. 154(b) by 299 days.

(21) Appl. No.: 15/534,026

(22) PCT Filed: Dec. 4, 2015

(86) PCT No.: PCT/JP2015/084108
§ 371 (c)(1),
(2) Date: Jun. 8, 2017

(87) PCT Pub. No.: WO2016/093162
PCT Pub. Date: Jun. 16, 2016

(65) Prior Publication Data
US 2018/0338865 A1 Nov. 29, 2018

(30) Foreign Application Priority Data
Dec. 10, 2014 (JP) ................. 2014-249785

(51) Int. Cl.
| | | |
|---|---|---|
| A61F 13/02 | (2006.01) | |
| B32B 27/00 | (2006.01) | |
| A61L 15/28 | (2006.01) | |
| A61L 15/24 | (2006.01) | |
| A61L 15/26 | (2006.01) | |
| B32B 27/32 | (2006.01) | |
| A61L 31/06 | (2006.01) | |
| A61L 31/04 | (2006.01) | |
| C08B 5/00 | (2006.01) | |

(52) U.S. Cl.
CPC .............. *A61F 13/02* (2013.01); *A61L 15/24* (2013.01); *A61L 15/26* (2013.01); *A61L 15/28* (2013.01); *A61L 31/042* (2013.01); *A61L 31/048* (2013.01); *A61L 31/06* (2013.01); *B32B 27/00* (2013.01); *B32B 27/32* (2013.01); *C08B 5/00* (2013.01)

(58) Field of Classification Search
CPC .... A61F 13/02; A61F 13/023; A61F 13/0226; A61F 13/0246; A61F 13/022; A61F 13/0236; A61F 13/00029; A61F 13/00038; A61F 13/0233; A61F 2013/00604; A61F 2013/00646; A61F 13/0266; A61F 2013/00229; A61F 2013/00263; C08B 5/00; A61L 15/28; A61L 15/24; A61L 31/048; A61L 31/06; A61L 31/042; A61L 15/26; B32B 27/32; B32B 27/00; A61Q 19/00; A61Q 19/007; A61Q 19/06; A61Q 17/00; B29C 51/14; B29C 65/5021; B29C 66/7212; B29C 63/02; B29C 66/723; B29C 43/003; B29C 45/0001; B29C 53/04; B29C 53/24; B29C 55/023; B29C 66/71
See application file for complete search history.

(56) References Cited

U.S. PATENT DOCUMENTS

| | | |
|---|---|---|
| 2008/0241203 A1 | 10/2008 | Morinaga et al. |
| 2010/0062258 A1 | 3/2010 | Takeoka et al. |
| 2014/0120144 A1* | 5/2014 | Abe .................. A61K 8/85 424/401 |

FOREIGN PATENT DOCUMENTS

| | | |
|---|---|---|
| JP | 2001-192337 A | 7/2001 |
| JP | 2003-153999 A | 5/2003 |
| JP | 2004-65780 A | 3/2004 |
| JP | 2012-187926 A | 10/2012 |
| WO | 2005/094915 A1 | 10/2005 |
| WO | 2012/014180 A1 | 2/2012 |
| WO | 2012/173198 A1 | 12/2012 |

* cited by examiner

*Primary Examiner* — Ophelia A Hawthorne
(74) *Attorney, Agent, or Firm* — DLA Piper LLP (US)

(57) ABSTRACT

A laminated film includes a polylactic acid-based resin layer and one or more acetylated hyaluronic acid layers laminated on a side of the polylactic acid-based resin layer, is highly flexible and easy to handle and, when stuck to an adherend with curved surface, the laminated film has excellent followability, adhesiveness and coating properties to the adherend, since the acetylated hyaluronic acid layer(s) can be removed easily with an aqueous solution from the polylactic acid-based resin layer in a thin film shape. The acetylated hyaluronic acid and the polylactic acid-based resin are biodegradable and, therefore, the laminated film is highly compatible with skin and organs such as visceral organs. The laminated film is optimally usable as a dermal material for external application such as a wound coating material, an adhesion inhibitor and skin care articles.

7 Claims, No Drawings

LAMINATED FILM AND MEDICAL SHEET

TECHNICAL FIELD

This disclosure relates to a laminated film having a polylactic acid-based resin layer and an acetylated hyaluronic acid layer, which is suitable for medical applications such as wound dressing membrane and adhesion-preventing membrane.

BACKGROUND

Adhesion of organs is one of the complications after open surgery such as in abdominal surgery or gynecology. Adhesion means a reformation with different organs wrongly contacting each other, sometimes caused in a wound healing process after a surgical operation although the organs should not contact each other in a normal situation. The adhesion which is often caused in an open surgery is usually asymptomatic. However, the adhesion might cause a serious complication such as pain, ileus and infertility although its frequency is low.

Once an adhesion is caused in a part, it cannot be treated noninvasively. So, the adhesion must be exfoliated by a surgical treatment when it has a serious complication such as ileus. Therefore, it is very important to appropriately treat a wounded part to not cause adhesion after the first operation.

Adhesion-preventing materials such as silicone, "TEFLON" (registered trademark) and polyurethane have been conventionally used to physically separate organs. However those materials are non-absorbable materials so that they remain on a biotissue surface as causing infection or inflammation as well as delaying tissue restoration.

To solve those problems, JP 2004-065780 A and JP 2001-192337 A disclose recent reports of adhesion-preventing materials made of natural macromolecules such as gelatin and collagen which are expected to be bioabsorbable. However, the gelatin or collagen should not be used in vivo because the antigenic telopeptide of gelatin and collagen can hardly be removed while they might cause a biological infection derived from prion contaminant. Further, cross-linkers to be added to enhance a strength and control the degradability should not be used in vivo in most cases.

The natural macromolecules might have poor strength although they have a high affinity to skin. Therefore, it has been necessary to make a cross-linked body with a cross-linker or ensure strength of the natural macromolecules with reinforcing material, wrapping gauze or the like. However, the reinforcing material might be impractical because of its complicated structure.

JP 2003-153999 A discloses a report of adhesion-preventing material comprising polysaccharides such as trehalose and sodium alginate having less risk of infection. However, a film material of polysaccharide might be impractical because it doesn't have a strength enough to firmly cover a wounded part without breakage or the like. WO 2005/094915 discloses a report of adhesion-preventing materials using hyaluronic acid. Although the soluble hyaluronic acid absorbs water in the body and gelates, the gel moves down by gravity as time goes by. Therefore, the effective ingredient might not remain on the affected area sufficiently or bacteria might grow in accumulated gel at the bottom to cause an infection.

Furthermore, there are some ways of using a blood product or chemical substance to make an adhesion-preventing material firmly contact to organs or the like, although the handling might be difficult with required control for highest safety.

JP 2012-187926 A discloses some ways of using a macromolecule structure having a laminate of water soluble resin layer and biodegradable resin layer made of polylactic acid or the like. However, the solubility and surgical handling (stickiness) of water soluble resin might not be sufficiently controlled.

Thus, there are many reports about materials with respect to adhesion preventing of tissues, but none of them have a sufficient ability as adhesion-preventing material. Thus, it could be helpful to provide a material to prevent the adhesion in a tissue-repairing time as maintaining the strength without the above-described problems.

Specifically, it could be helpful to provide a laminated film comprising acetylated hyaluronic acid layer and a polylactic acid-based resin layer that is highly biocompatible and easy to handle, has good pasting ability and contact to an organ tissue and rarely induces infections.

SUMMARY

We thus provide:

(1) A laminated film comprising one or more layers of acetylated hyaluronic acid layer having a thickness of 1 μm or more and 100 μm or less, provided on a side of a polylactic acid-based resin layer having a thickness of 10 nm or more and 500 nm or less.
(2) The laminated film according to (1), wherein the acetylated hyaluronic acid has an acetylation degree of 0.1 or more and 0.9 or less.
(3) The laminated film according to (1) or (2), wherein the acetylated hyaluronic acid has a weight average molecular weight of 100,000 or more and 3,000,000 or less in terms of hyaluronic acid.
(4) A medical sheet comprising the laminated film according to any one of (1) to (3).

Our laminated film, which comprises one or more layers of an acetylated hyaluronic acid provided on a side of a polylactic acid-based resin layer, is highly flexible and easy to handle and, when pasted on an adherend with a curved surface, the laminated film exhibits excellent followability, contact and coating properties to the adherend since the acetylated hyaluronic acid layer can be removed easily with an aqueous solution from the polylactic acid-based resin layer in a thin film shape. Further, the acetylated hyaluronic acid and the polylactic acid-based resin are biodegradable and, therefore, the laminated film is highly compatible with skin and organs such as visceral organs. Thus, the laminated film is suitable as an external dermal material such as wound dressing, adhesion-preventing material and skin care article.

The number of substituted acetyl groups and weight average molecular weight of acetylated hyaluronic acid can also be selected properly to control characteristics such as sticky texture, solubility to aqueous solution and handling ability of the laminated film. Further, bacteria are less proliferous in an adhesion-preventing material made of acetylated hyaluronic acid than in other general water soluble resins so that infection is prevented.

The polylactic acid-based resin layer separated by aqueous solution from the acetylated hyaluronic acid is clear enough to obscure a pasted surface so that the polylactic acid-based resin layer can be used as adhesive plaster to be pasted on skins, in addition to surgical usage.

The polylactic acid-based resin layer and/or acetylated hyaluronic acid layer can hold and release various drugs to be used for drug delivery system.

DETAILED DESCRIPTION

"Film" means a structure extending in two dimensions, including sheet, plate, discontinuous film or the like.

Polylactic Acid-Based Resin

It is preferable that the polylactic acid-based resin has a weight average molecular weight of 50,000 or more. It is preferably 80,000 to 1,000,000 and more preferably 100,000 to 500,000. The weight average molecular weight is calculated by polystyrene (PS) conversion method from results of measurement performed with chloroform solvent by gel permeation chromatography (GPC). With polylactic acid-based resin having a weight average molecular weight of 50,000 or more, the polylactic acid-based resin layer can be excellent in mechanical characteristics.

To improve the solubility in preparing a film coating liquid, crystalline homopolymer of lactic acid-based resin and amorphous homopolymer of lactic acid-based resin can be added to the polylactic acid-based resin. The amorphous homopolymer of lactic acid-based resin can be added to the extent that the desired effect is maintained. To give relatively high heat resistance to the polylactic acid-based resin layer, it is preferable that at least one kind of polylactic acid-based resins has an optical purity of 95% or more.

It is preferable that the polylactic acid-based resin has a primary component of poly L-lactic acid (L body) and/or poly D-lactic acid (D body). The primary component means a component derived from lactic acid contained by 70 mol % to 100 mol % in total 100 mol % of monomer components constituting polylactic acid-based resin. It is preferably a homopolymer of lactic acid-based resin substantively consisting of poly L-lactic acid and/or poly D-lactic acid only.

It is preferable that the poly D-lactic acid of 4 to 50 mol % is contained in the polylactic acid-based resin. It is more preferable that the content is 6 to 13 mol %. The poly-D lactic acid content of less than 4 mol % might deteriorate the solubility to organic solvent to make it difficult to prepare a coating agent. The content of more than 50 mol % might make it hard to be metabolized although it may vary among different individuals.

The polylactic acid-based resin may be L-lactic acid or D-lactic acid, or may be a copolymerized polylactic acid-based resin which is copolymerized with another monomer component having ester formation ability. The monomer component to be copolymerized may be hydroxy carboxylic acids such as glycolic acid, 3-hydroxybutyric acid, 4-hydroxybutyric acid, 4-hydroxy valeric acid and 6-hydroxy caproic acid, a compound of which molecule contains hydroxyl groups such as ethylene glycol, propylene glycol, butanediol, neopentylglycol, polyethylene glycol, glycerin, pentaerythritol and derivative thereof, a compound of which molecule contains carboxylic acid groups such as succinic acid, adipic acid, sebacic acid, fumaric acid, terephthalic acid, isophthalic acid, 2,6-naphthalenedicarboxylic acid, 5-sodium sulfoisophthalic acid, 5-tetrabutyl phosphonium sulfoisophthalic acid and derivative thereof. Among the above-described copolymerization components, it is preferable to choose a component having biodegradability as usage. It is preferable that the copolymerization component other than the polylactic acid is contained by 30 mol % or less in total 100 mol % of the monomer components constituting the polylactic acid-based resin.

The polylactic acid-based resin may be produced by methods to be explained later, such as direct polymerization method starting from lactic acid and a ring-opening polymerization method using lactide.

From viewpoints of good durability (long-term storage ability) and suppression of strength degradation derived from hydrolysis, it is preferable that the polylactic acid-based resin has a carboxyl terminal concentration of 30 equivalent/$10^3$ kg or less. It is preferably 20 equivalent/$10^3$ kg or less, and is more preferably 10 equivalent/$10^3$ kg or less. The carboxyl terminal concentration of 30 equivalent/$10^3$ kg or less can make the polylactic acid-based resin durable practically because of such a sufficiently low carboxyl terminal concentration to be a self catalyst of the hydrolysis. The carboxyl terminal concentration may be close to 0 equivalent with no limit.

To control the carboxyl terminal concentration in the polylactic acid-based resin to 30 equivalent/$10^3$ kg or less, it is possible to employ a method to appropriately choose a catalyst or heat history for synthesizing the polylactic acid-based resin, a method to reduce the heat history by decreasing the temperature or decreasing the time of the laminating process, a method of blocking the carboxyl terminal by a reactive compound or the like.

In the method of blocking the carboxyl terminal by a reactive compound, it is preferable that the carboxyl terminal in the polylactic acid-based resin is at least partially blocked. It is more preferable that the carboxyl terminal is wholly blocked. The reactive compound may be a condensing reactive compound such as aliphatic alcohol and amide compound, or an addition reactive compound such as carbodiimide compound, epoxy compound and oxazoline compound. It is preferably the addition reactive compound that hardly produces a by-product. From a viewpoint of reaction efficiency, it is preferably the carbodiimide compound above all.

To improve mechanical strength, it is possible that the polylactic acid-based resin layer contains 2 mass % or more and 20 mass % or less of an impact modifier in total 100 mass % of polylactic acid-based resin layer. The content is preferably 2.5 mass % or more and 15 mass % or less. Basically, the more the content of the impact modifier is, the more the effect of impact modification improves. However the content of more than 20 mass % might not have a greatly improved mechanical strength.

It is preferable that the impact modifier used to improve the impact resistance is aliphatic polyester or aliphatic aromatic polyester other than the polylactic acid-based resin because they have a good dispersibility in the polylactic acid-based resin so that even small amount of them achieves a high effect.

Aliphatic polyester or aliphatic aromatic polyester other than the polylactic acid-based resin may be polyglycolic acid, 3-hydroxybutyric acid polymer, 4-hydroxybutyric acid polymer, 4-hydroxy valeric acid polymer, 3-hydroxy hexanoic acid polymer, polycaprolactone, polyethylene adipate, polyethylene succinate, polybutylene succinate, polybutylene succinate adipate, polybutylene adipate-butylene terephthalate copolymer or the like.

To improve mechanical strength as maintaining biodegradability, it is preferable that the aliphatic polyester other than the polylactic acid-based resin is polybutylene succinate-based resin. It is more preferable to employ polybutylene succinate or polybutylene succinate adipate having a great advantage of improving mechanical strength and a good compatibility to the polylactic acid-based resin.

It is preferable that the polybutylene succinate-based resin has a weight average molecular weight of 100,000 to 300,000. The polybutylene succinate-based resin can be produced by polycondensation of 1,4-butanediol and succinic acid.

The polylactic acid-based resin can be produced by the following method from raw materials of a lactic acid component of L-lactic acid or D-lactic acid together with hydroxy carboxylic acid other than the lactic acid component. It is possible that the raw materials include a cyclic ester intermediate of hydroxy carboxylic acid such as lactide and glycolide. It is also possible to employ a dicarbon acid or glycol.

The polylactic acid-based resin can be produced by a method of dehydration condensation directly from the raw materials or a method of ring-opening polymerization of the cyclic ester intermediate. As an example of the direct dehydration condensation, high-molecular weight polymer can be obtained by a azeotropic dehydration condensation method with a lactic acid and optionally with a hydroxy carboxylic acid, preferably in the presence of an organic solvent such as phenyl ether-based solvent particularly so that the solvent distilled by the azeotrope is dehydrated to make a substantially anhydrous solvent to be recycled to the reaction system to polymerize the lactic acid.

It is known that the high-molecular weight polymer can be obtained by a ring-opening polymerization with a cyclic ester intermediate such as lactide with tin octylate catalyst or the like under reduced pressure. To obtain the polymer having less amount of lactide, a condition may be adjusted to remove water and low-molecular weight compound in organic solvent at the time of heat refluxing, a depolymerization may be suppressed by deactivating a catalyst after finishing the polymerization reaction, or the polymer product may be subject to a heat treatment.

From a viewpoint of followability to a shape of adherend, it is preferable that the polylactic acid-based resin has a thickness of 10 nm or more and 500 nm or less. It is more preferably 10 nm or more and 100 nm or less. The thickness of less than 10 nm might make retention of shape difficult while the thickness of more than 500 nm might cause wrinkles on the adherend.

It is possible that an additive is contained by 30 mass % or less in total 100 mass % of the polylactic acid-based resin layer, to the extent of maintaining the desired effect. The additive may be an antioxidant, weathering agent, heat stabilizer, lubricant, crystalline nucleus agent, ultraviolet absorbent, coloring agent or the like. Without the lower limit, it is possible that the additive may be contained by 0 mass % in total 100 mass % of the polylactic acid-based resin layer. To the extent of maintaining transparency, it is possible that inorganic or organic particles are contained by 20 mass % or less in total 100 mass % of the polylactic acid-based resin layer. The particles may be made of calcium carbonate, titanium oxide, silicon oxide, calcium fluoride, lithium fluoride, alumina, barium sulfate, zirconia or calcium phosphate, or may be cross-linked polystyrene-based particles, metal nanoparticles or the like. Without the lower limit, it is possible that the inorganic or organic particles may be contained by 0 mass % in total 100 mass % of the polylactic acid-based resin layer.

It is possible that at least one side of the polylactic acid-based resin layer is provided with a bioabsorbable material layer made of gelatin, collagen, hyaluronic acid, chitosan, synthetic polypeptide or the like, to the extent of maintaining the desired effect.

Acetylated Hyaluronic Acid

The acetylated hyaluronic acid may be produced by a method in which powdered hyaluronic acid is dispersed in acetic acid to which anhydrous trifluoroacetic acid catalyst is added to progress the acetylation reaction. Alternatively, the production method may be such that powdered hyaluronic acid is dispersed in acetic acid to which p-toluenesulfonic acid and then acetic anhydride are added to progress the acetylation reaction, or such that hyaluronic acid is suspended in acetic acid anhydride to which concentrated sulfuric acid is added to progress the acetylation reaction.

To obtain purified white powder of acetylated hyaluronic acid, it is possible to add pyridine to the product to be neutralized and stirred in added water to completely dissolve the precipitate, to which acetone is added gradually as stirring to precipitate the product, which is centrifuged to separate another precipitate to be dissolved in sodium acetate and then precipitated with acetone. Finally, it is washed with acetone to be completely anhydrated, and then dried under reduced pressure.

The acetylation degree (proportion of acetylation-modified hyaluronic acid) of the acetylated hyaluronic acid can be determined by NMR. The hyaluronic acid is chemically modified with acetic acid to obtain acetylated hyaluronic acid, of which NMR measured is integrated to calculate the acetylation degree.

Acetylation degree=(acetyl group peak integral/3)/{(hydroxyl group peak integral)+(acetyl group peak integral/3)}

It is preferable that the acetylated hyaluronic acid has an acetylation degree of 0.1 or more and 0.9 or less. It is more preferably 0.3 or more and less than 0.7, preferably 0.5 or more and less than 0.7. The acetylation degree of 0.1 or more can easily retain a shape for good handling with desirable degradability and solubility to solution while the acetylation degree of 0.9 or less can enhance preparation without too much slowing the dissolution to aqueous solution.

It is preferable that the acetylated hyaluronic acid has a weight average molecular weight determined by liquid chromatography (HPLC) method of 100,000 or more and 3,000,000 or less in terms of hyaluronic acid. It is preferably 800,000 or more and 1,800,000 or less, preferably 800,000 or more and 1,200,000 or less. The weight average molecular weight of acetylated hyaluronic acid of 100,000 or more can easily retain a shape for good handling with desirable degradability and solubility to solution while the weight average molecular weight of 3,000,000 or less can enhance preparation without too much slowing the dissolution to aqueous solution. The value in terms of hyaluronic acid is "molecular weight in terms of standard polymer" of the sample polymer (acetylated hyaluronic acid) calculated from a graph (calibration curve) showing the relation between molecular weight and elution time which is obtained by analyzing the sample polymer (acetylated hyaluronic acid) under the same condition as the standard polymers (some kinds of hyaluronic acids of which molecular weights are known).

Two or more kinds of acetylated hyaluronic acids having different weight average molecular weights may be used together. It is preferable to employ a low-molecular weight acetylated hyaluronic acid having a weight average molecular weight of 100,000 or more and less than 1,000,000, together with a high-molecular weight acetylated hyaluronic acid having a weight average molecular weight of 1,000,000 or more and less than 3,000,000. Such employed two or more kinds of acetylated hyaluronic acids can make a coating having a good contact to the polylactic acid-based resin layer as well as a high mechanical strength and re-solubility to aqueous solution.

An additive may be contained by 30 mass % or less in total 100 mass % of acetylated hyaluronic acid layer to the extent of maintaining the desired effect. Without the lower limit, it may be 0 mass %. The additive may be antioxidant, weathering agent, heat stabilizer, lubricant, crystalline nucleus agent, ultraviolet absorbent, coloring agent or the like. To the extent of maintaining the desired effect, it is possible that inorganic or organic particles are contained by 20 mass % or less. Without the lower limit, it may be 0 mass %. The particles may be made of calcium carbonate, titanium oxide, silicon oxide, calcium fluoride, lithium fluoride, alumina, barium sulfate, zirconia or calcium phosphate, or may be cross-linked polystyrene-based particles, metal nanoparticles or the like.

It is preferable that the acetylated hyaluronic acid layer has a thickness of 1 μm or more and 100 μm or less, preferably 1 μm or more and 60 μm or less. The thickness of the acetylated hyaluronic acid layer of less than 1 μm might have an excessively short dissolution time while the thickness of more than 100 μm might deteriorate the ability of pasting to organ. In two or more acetylated hyaluronic acid layers, the thickness range of 1 μm to 100 μm should be applied to all the acetylated hyaluronic acid layers.

It is possible that there are two or more layers or only one layer provided for the acetylated hyaluronic acid layer. The two or more layers can easily control the dissolution time and pasting ability by providing layers having different acetylation degrees and molecular weights.

Base Material

The base material in laminated film production method to be mentioned later will be explained. The base material is used to form the acetylated hyaluronic acid layer and polylactic acid-based resin layer.

The base material may be a film made of silicon, glass, metal or macromolecule. It is preferably a silicon substrate from a viewpoint of smoothness, while it is preferably a base film consisting of macromolecule from a viewpoint of productivity.

The base film may be made of a polyolefin such as polyethylene and polypropylene, a polyester such as polyethylene terephthalate, polybutylene terephthalate, polyethylene-2,6-naphthalate, a polyamide such as nylon 6 and nylon 12 and, alternatively, polyvinyl chloride, ethylene vinyl acetate copolymer or its saponificate, polystyrene, polycarbonate, polysulfone, a polyphenylene oxide, polyphenylene sulfide, aromatic polyamide, polyimide, polyamide-imide, cellulose, cellulose acetate, polyvinylidene chloride, polyacrylonitrile, polyvinyl alcohol, copolymer thereof or the like. From viewpoints of good contact between the acetylated hyaluronic acid layer and the polylactic acid-based resin layer as well as uniform thickness of laminated film, it is preferable that the base film is made of a polyester such as polyethylene terephthalate or a polyolefin such as polyethylene and polypropylene. The polyester such as polyethylene terephthalate is particularly preferable because of a high wet tension on the surface.

It is more preferable that the base film is subject to a surface treatment such as corona discharge processing, flame processing, plasma processing and ultraviolet irradiation processing before forming a coating film of the acetylated hyaluronic acid layer or polylactic acid-based resin layer.

The base film may be unstretched film, uniaxially stretched film or biaxially stretched film. From viewpoints of dimension stability and mechanical properties, it is preferable to employ a biaxially stretched film.

The base film may contain an additive such as antioxidant, weathering agent, heat stabilizer, lubricant, crystalline nucleus agent, ultraviolet absorbent and coloring agent. To the extent of not markedly spoiling the surface smoothness, it may contain inorganic or organic particles such as particles made of talc, kaolinite, calcium carbonate, titanium oxide, silicon oxide, calcium fluoride, lithium fluoride, alumina, barium sulfate, zirconia, mica, calcium phosphate and cross-linked polystyrene.

It is preferable that the inorganic or organic particles contained as an additive have an average particle diameter of 0.001 to 10 μm, preferably 0.003 to 5 μm. The average particle diameter means a number average particle diameter measured from a transmission electron microscopic image of magnification of ×10,000-100,000. It is preferable that the base film is transparent. It is preferable that the base film has a total light transmittance of 40% or more. It is more preferably 60% or more and 100% or less, without particular upper limit. It is preferable that the base film has a haze of 20% or less, preferably 15% or less. The haze of 20% or less makes it easy to inspect the laminated acetylated hyaluronic acid layer and polylactic acid-based resin layer to detect impurities with an optical test device. Without the lower limit, the haze can be close to 0%.

It is preferable that the base film has a thickness of 2 to 1,000 μm. It is more preferably 10 to 500 μm from a viewpoint of economic efficiency.

Production Method

Hereinafter, typical production method of the laminated film will be explained.

Production Method of Laminated Film

The following methods are examples of method to provide a laminated film on a side of the base material.

(i) Method of laminating a polylactic acid-based resin layer on an acetylated hyaluronic acid layer after having laminated the acetylated hyaluronic acid layer on the base film (ii) Method of laminating a polylactic acid-based resin layer on an acetylated hyaluronic acid layer after having laminated 2 or more layers of the acetylated hyaluronic acid layer on the base film (iii) Method of laminating an acetylated hyaluronic acid layer on a polylactic acid-based resin layer after having laminated the polylactic acid-based resin layer on the base film (iv) Method of laminating 2 or more layers of acetylated hyaluronic acid layer on a polylactic acid-based resin layer after having laminated the polylactic acid-based resin layer on the base film The lamination method may be spin coating, gravure coating, direct lip coating, slot coating, comma coating, ink-jet or silkscreen print or the like. The base material may be silicon substrate, glass plate, metal plate, plastic film or the like. To improve wettability and contact of the coating agent, the base film before coating can be subject to an adhesion promotion processing such as corona discharge processing in atmosphere of air, nitrogen gas, mixed gas of nitrogen/carbon dioxide or the like, plasma processing under reduced pressure, flame processing, ultraviolet processing or the like. It is possible that the base material is subject to an anchor processing using anchor treatment agent such as urethane resin, epoxy resin and polyethyleneimine.

To suppress too strong contact, the base material may be provided with a release layer, which may be a hydrophobic layer to contact the acetylated hyaluronic acid layer, or a hydrophilic layer to contact the polylactic acid-based resin layer. The resin to constitute the hydrophobic layer may be a polylactic acid resin while the resin to constitute the hydrophilic layer may be polyvinyl alcohol.

The following methods are examples of method to produce the laminated film provided with a release layer on the base film.

(v) Method of laminating a polylactic acid-based resin layer on an acetylated hyaluronic acid layer laminated on a hydrophobic layer after having provided the hydrophobic layer on the base material (vi) Method of laminating a polylactic acid-based resin layer on an acetylated hyaluronic acid layer of which 2 or more layers are laminated on a hydrophobic layer after having provided the hydrophobic layer on the base material (vii) Method of laminating an acetylated hyaluronic acid layer on a polylactic acid-based resin layer laminated on a hydrophilic layer after having provided the hydrophilic layer on the base material (viii) Method of laminating 2 or more layers of acetylated hyaluronic acid layer on a polylactic acid-based resin layer laminated on a hydrophilic layer after having provided the hydrophilic layer on the base material From a viewpoint of economic efficiency, the base film can be a plastic film particularly having a good surface smoothness. To employ a biaxially stretched film made of polyester such as polyethylene terephthalate or polyolefin such as polypropylene as a base material, an off-line coating may be performed after film forming process of the biaxially stretched film. Alternatively, an in-line coating may be performed in the film forming process of the biaxially stretched film.

It is preferable that the in-line coating is performed before heat fixation of the film. Heat fixation means that the film is crystalized by a heat treatment at a temperature kept higher than the stretching temperature of the stretched film and kept lower than the melting point of the film. It is preferable that the coating is performed on an unstretched film or a film that has just been stretched biaxially or uniaxially in the longitudinal or lateral direction stretched film. It is more preferable that the coating is performed on a film that has just been stretched uniaxially, preferably the film is further stretched at least uniaxially and then subject to heat fixation process. The coating film may be dried by a method such as heating roll contact method, heat medium (air, oil or the like) contact method, infrared heating method, microwave heating method or the like.

A high-speed thin film coating can be performed by the off-line coating on the base film. It is preferable that a solution of components of coating dispersed in a solvent is subject to a coating process such as spin coating, gravure coating, reverse coating, spray coating, kiss coating, comma coating, die coating, knife coating, air knife coating or metering bar coating. It is preferable that the coating of the acetylated hyaluronic acid is dried at 60° C. to 180° C. for the off-line coating or 80° C. to 250° C. for the in-line coating. It is preferable that the drying time is 1 to 60 sec, preferably 3 to 30 sec.

It is preferable that the coating of the polylactic acid-based resin is dried at 60° C. to 110° C. for the off-line coating or 80° C. to 180° C. for the in-line coating. It is preferable that the drying time is 1 sec to 60 sec, preferably 3 sec to 30 sec.

To prepare the laminated film of acetylated hyaluronic acid layer and polylactic acid-based resin layer, it is preferable that an interface between the base material and acetylated hyaluronic acid layer or polylactic acid-based resin is mechanically exfoliated with a tweezer or the like. When it is hardly exfoliated by such a method, it is possible that an adhesive tape is pasted firmly on the outermost layer at the side opposite to the base material so that the interface can be exfoliated forcibly.

In the base material provided with a release layer (hydrophobic layer or hydrophilic layer), it is preferable that an interface between the release layer and acetylated hyaluronic acid layer or polylactic acid-based resin is mechanically exfoliated with a tweezer or the like to prepare the laminated film of acetylated hyaluronic acid layer and polylactic acid-based resin layer.

Coating Agent Containing Acetylated Hyaluronic Acid

It is preferable that the coating agent containing acetylated hyaluronic acid contains homogeneously dissolved components. It is preferable that the solvent is water or a mixed solution of water and lower alcohol. It is more preferable that it is the mixed solution of water and lower alcohol.

From viewpoints of viscosity, drying efficiency and coatability, it is preferable that the coating agent containing the acetylated hyaluronic acid has a solid content concentration of 0.5 mass % or more and 15 mass % or less. The solid content concentration of 15 mass % or less can make the solution viscosity not too high to control the thickness of the acetylated hyaluronic acid layer. The solid content concentration of 0.5 mass % or less makes it easy to add a hydrophilic volatile solvent which has a low boiling point to the coating agent solvent, or to dry the coating film at the temperature higher than the water boiling point.

To impart coatability, the mixed solvent may contain another water-soluble organic compound as a third component to the extent of maintaining the stability of coating agent containing the acetylated hyaluronic acid. The water-soluble organic compound may be an alcohol such as methanol, ethanol, n-propanol and isopropanol, a glycol such as ethylene glycol and propylene glycol, a glycol derivative such as methyl cellosolve, ethyl cellosolve and n-butyl cellosolve, a polyvalent alcohol such as glycerin and wax, an ether such as dioxane, an ester such as ethyl acetate, a ketone such as methyl ethyl ketone or the like. It is preferable that the dispersion solution has a pH of 2 to 11 from a viewpoint of stability of the solution.

Coating Agent Containing Polylactic Acid-Based Resin

It is preferable that the coating agent containing polylactic acid-based resin contains homogeneously dissolved components. It is preferable that the solvent is a single solvent or a mixed solution consisting of 2 or more kinds of solvent, selected from a group of butyl alcohol, chloroform, cyclohexane, acetonitrile, dichloromethane, dichloroethane, ethyl acetate, ethyl ether, dipropyl ether and toluene. From viewpoints of productivity and handling ability, the solvent is particularly preferably ethyl acetate.

From viewpoints of viscosity, drying efficiency and coatability, it is preferable that the coating agent containing the polylactic acid-based resin has a solid content concentration of 1.0 mass % or more and 10 mass % or less.

To impart coatability, the solution may contain another water-soluble organic compound as a third component to the extent of maintaining the stability of coating agent containing the polylactic acid-based resin.

Preparation Method of Coating Agent

Although the preparation method of the coating agent containing the acetylated hyaluronic acid or the polylactic acid-based resin is not particularly limited, when an additive such as cross-linker and particle is added to the extent of maintaining the desired effect, it is preferable that the additive and a resin are homogeneously dispersed in the coating agent. As needed, it is possible that the solubility of resin is increased by raising temperature of the solvent by heater or the like. It is also possible that a mechanical forced dispersing processing is performed by a device such as homomixer capable of generating shear force and shear stress, jet type agitator, ball mill, bead mill, kneader, sand mill and three-rollers mill.

Usage of Laminated Film

The laminated film is flexible enough to be pasted on a flat surface or a highly-curved surface. Once the acetylated hyaluronic acid layer is removed from the film by water or saline, the polylactic acid-based resin can be pasted on any surface. Particularly for surgery, the film can be pasted on organs or the like so that biotissues are prevented from adhering to each other. Further, the acetylated hyaluronic acid can suppress bacterial growth better in comparison with other general-purpose water-soluble resin.

Use Application

The laminated film is suitably used for medical applications such as wound dressing membrane and adhesion-preventing membrane available even in vivo or in a wet environment. Therefore, the laminated film is suitably applicable as a medical sheet, such as wound dressing membrane and adhesion-preventing membrane.

EXAMPLES

Evaluation Method of Characteristics
(1) Acetylation Degree

The acetylation degree is determined from integral values of NMR for acetyl group and hydroxyl group according to the following formula.

Acetylation degree=(acetyl group peak integral/3)/{(hydroxyl group peak integral)+(acetyl group peak integral/3)}

(2) Weight Average Molecular Weight of Acetylated Hyaluronic Acid

The weight average molecular weight in terms of hyaluronic acid is determined by liquid chromatography (HPLC) method under the following conditions.
Device: ACQUITY UPLC system (made by Nihon Waters K.K.)
Column: Shodex Ionpak KS806 (made by Shimadzu Corporation)
Moving phase: 0.2 mol/L sodium chloride aqueous solution
Flow rate: 1.0 mL/min
Detector: ACQUITY UPLC RID detector (made by Nihon Waters K.K.)
(3) Thickness of Polylactic Acid-Based Resin Layer The acetylated hyaluronic acid layer dissolved in water is transferred to a silicon substrate. The layer thickness is measured with an atom force microscope (NanoScale Hybrid Microscope made by Keyence corporation, "VN-8000", tapping mode).
(4) Thickness of Acetylated Hyaluronic Acid Layer A cross section, which has been cut out with a microtome (Retoratome REM-710 made by Yamato Kohki Industrial Co., Ltd.) from the laminated film without collapsing in the thickness direction, is observed with a transmission electron microscope (made by Hitachi, Ltd., TEM H7100) as adjusting the magnification between 250 to 5,000 so that each acetylated hyaluronic layer thickness occupies 50% or more of proportion in the vertical direction of image to measure the thickness.

(5) Evaluation of Solubility of Acetylated Hyaluronic Acid Layer

The height between the surface of test piece (1.5 cm×1.0 cm rectangle) and the tip of the burette is adjusted to 10 mm. The dissolution ending time is determined from the starting time when saline (1 mL) is dropped from the burette onto the acetylated hyaluronic acid layer. The dissolution means that a shape of part having an area of 50% or more of the initial area (1.5 cm×1.0 cm rectangle) cannot be maintained and collapses, as visually observed with respect to various aspects.
Evaluation classification A: Time of 10 sec or more and less than 5 min is required until the dissolution finishes.
Evaluation classification B: 5 min or more
Evaluation classification C: Less than 10 sec
(6) Survival Rate and Pasting Ability in Test for Inducing Microorganism Development in Mouse Abdominal Cavity Male mice (made by Japan SLC, Inc., C57BL6, 22-25 g in weight, eight mice) of which age is 8 weeks or more and 9 weeks or less are anesthetized with ether to open and expose their abdomens. Test pieces (1.5 cm×1.0 cm rectangle) are pasted without forming serosa defective injury. After the pasting, *Escherichia coli* is seeded in abdominal cavity by $4\times10^8$ CFU (Colony Forming Unit) so that the survival rate within 1 week after surgery and the number of bacteria in the abdominal cavity on 1 day after the surgery are determined. The ability to induce microorganism development is evaluated according to the following standards.
Evaluation classification A: CFU of *Escherichia coli* is less than 1.5 times the value of the Reference Example
Evaluation classification B: CFU of *Escherichia coli* is 1.5 times or more and less than 10 times the value of the Reference Example
Evaluation classification C: CFU of *Escherichia coli* is 10 times or more the value of the Reference Example The survival rate is evaluated according to the following standards.
Evaluation classification A: 60% or more and 100% or less
Evaluation classification B: 20% or more and less than 60%
Evaluation classification C: Less than 20%

The pasting ability is evaluated by visually observing according to the following standards.
Evaluation classification A: 70% or more and 100% or less of test piece area is contacted as following the organ
Evaluation classification B: 50% or more and less than 70% of test piece area is contacted as following the organ
Evaluation classification C: Only less than 50% of test piece area is contacted as following the organ
Spin Coater Employed
Opticoat MS-A150 made by Misaka Co., Ltd.
Base Material Employed
Silicon Substrate:
P type silicon wafer (diameter 100±0.5 mm, thickness 525±25 μm, oxide film 200 nm, crystal surface (100)) made by KST World corp. is cut into size of 40 mm×40 mm. Before using, the silicon substrate is immersed for 10 min in a liquid mixed by volume ratio of 3:1 with sulfuric acid (98 mass %) and oxygenated water (mass %), and then is washed with deionized water (specific resistance: 18 Ωcm).
Acetylated Hyaluronic Acid Employed The acetylated hyaluronic acid is prepared from acetic acid and hyaluronic acid (made by Shiseido Company) as follows.
AcHA-1

Acetylated hyaluronic acid having acetylation degree of 0.6 prepared from HA9N (hyaluronic acid made by Shiseido Company, weight average molecular weight 990,000)

AcHA-2

Acetylated hyaluronic acid having acetylation degree of 0.4 prepared from HA12N (hyaluronic acid made by Shiseido Company, weight average molecular weight 1,350,000)

AcHA-3

Acetylated hyaluronic acid having acetylation degree of 0.2 prepared from HA20N (hyaluronic acid made by Shiseido Company, weight average molecular weight 2,300,000)

AcHA-4

Acetylated hyaluronic acid having acetylation degree of 0.9 prepared from HA9N (hyaluronic acid made by Shiseido Company, weight average molecular weight 990,000) Polyvinyl alcohol resin employed

PVA-1

Polyvinyl alcohol having saponification degree of 88 mol % and viscosity of 5 mPa·s (4 mass % aqueous solution, 20° C.)

Polylactic Acid-Based Resin Employed

PLA-1:

Poly L-lactic acid-D-lactic acid copolymer-based resin (PURASORB (registered trademark) PDL20 made by PURAC Company) having poly D-lactic acid content of 50 mol % and weight average molecular weight of 140,000 in terms of PS with no melting point (amorphous)

Example 1

A hydrophobic layer was provided on the surface of silicon substrate by spin coating (4,000 rpm, 20 sec) on the silicon substrate to be dried (60° C. for 30 sec) so that ethyl acetate solution of PLA-1 had dry thickness of 100 nm. Next, an acetylated hyaluronic acid layer was formed by spin coating (4,000 rpm) and drying heating (60° C., 30 sec) on the hydrophobic layer so that acetylated hyaluronic acid solution prepared by dissolving AcHA-1 in a solvent having a weight ratio of water/ethanol=30/70 had dry thickness of 50 μm. Then, a polylactic acid-based resin layer was formed by spin coating (4,000 rpm) and drying heating (60° C., 30 sec) on the acetylated hyaluronic acid layer so that the ethyl acetate solution of PLA-1 had dry thickness of 100 nm. The acetylated hyaluronic acid layer/polylactic acid-based resin layer were mechanically exfoliated from the hydrophobic layer to obtain a laminated film. Table 1 shows evaluation results. The above-described solubility evaluation was performed to find that the layer was well dissolved with 1 mL of saline. The number of bacteria in the abdominal cavity on 1 day after the surgery was $1.5 \times 10^6$ CFU while the survival rate within 1 week after surgery was 67%, which was in the same level as Reference Example supposed not to induce the bacterial infection.

Example 2

A laminated film was obtained by the same method as Example 1, except that the acetylated hyaluronic acid layer had dry thickness of 1 μm. Table 1 shows evaluation results.

Example 3

A laminated film was obtained by the same method as Example 1, except that the acetylated hyaluronic acid layer had dry thickness of 100 μm. Table 1 shows evaluation results.

Example 4

A laminated film was obtained by the same method as Example 1, except that the polylactic acid-based resin layer had dry thickness of 10 nm. Table 1 shows evaluation results.

Example 5

A laminated film was obtained by the same method as Example 1, except that the polylactic acid-based resin layer had dry thickness of 500 nm. Table 1 shows evaluation results.

Example 6

A laminated film was obtained by the same method as Example 1, except that the acetylated hyaluronic acid layer was formed with AcHA-2 instead of AcHA-1. Table 1 shows evaluation results.

Example 7

A laminated film was obtained by the same method as Example 1, except that the acetylated hyaluronic acid layer was formed with AcHA-3 instead of AcHA-1. Table 1 shows evaluation results.

Example 8

A laminated film was obtained by the same method as Example 1, except that the acetylated hyaluronic acid layer was formed with AcHA-4 instead of AcHA-1. Table 1 shows evaluation results.

Comparative Example 1

A laminated film was obtained by the same method as Example 1, except that the acetylated hyaluronic acid layer had dry thickness of 0.1 μm. Table 2 shows evaluation results.

Comparative Example 2

A laminated film was obtained by the same method as Example 1, except that the acetylated hyaluronic acid layer had dry thickness of 250 μm. Table 2 shows evaluation results.

Comparative Example 3

A laminated film was obtained by the same method as Example 1, except that the polylactic acid-based resin layer had dry thickness of 5 nm. Table 2 shows evaluation results.

Comparative Example 4

A laminated film was obtained by the same method as Example 1, except that the polylactic acid-based resin layer had dry thickness of 5,000 nm. Table 2 shows evaluation results.

Comparative Example 5

A laminated film was obtained by the same method as Example 1, except that the acetylated hyaluronic acid layer was formed with hyaluronic acid HA12N instead of AcHA-1. Table 3 shows evaluation results.

Comparative Example 6

A single film (thickness 50 μm) of hyaluronic acid HA12N was obtained by the same method as Comparative Example 5, except for not forming the polylactic acid-based resin layer. Table 3 shows evaluation results. The number of bacteria in the abdominal cavity on 1 day after the surgery was $16 \times 10^6$ CFU (Evaluation classification C) while the survival rate within 1 week after surgery was 18%. Thus obtained film cannot be applied to infected wound because it might induce the bacterial infection.

Reference Example

Survival Rate in Test of Inducing Microorganism Development in Mouse Abdominal Cavity Male mice (made by Japan SLC, Inc., C57BL6, 22-25 g in weight, eight mice) of which age was 8 weeks or more and 9 weeks or less were anesthetized with ether to open and expose their abdomens, and then *Escherichia coli* was seeded in abdominal cavity by $4 \times 10^8$ CFU (Colony Forming Unit) so that the survival rate within 1 week after surgery and the number of bacteria in the abdominal cavity on 1 day after the surgery were determined. The number of bacteria in the abdominal cavity on 1 day after the surgery was $1.5 \times 10^6$ CFU (standard value) while the survival rate within 1 week after surgery was 57%.

TABLE 3

| | | Comparative Example 5 | Comparative Example 6 |
|---|---|---|---|
| Thickness | Hyaluronic acid layer [μm] | 50 | 50 |
| | Polylactic acid-based resin layer [nm] | 100 | — |
| Resin | Hyaluronic acid | HA12N | HA12N |
| Characteristics | Solubility | C | C |
| | Ability to induce microorganism development | C | C |
| | Mouse survival rate | C | C |
| | Pasting ability | A | A |

INDUSTRIAL APPLICATIONS

The laminated film is flexible enough to be pasted on a flat surface or a highly-curved surface. Once the acetylated hyaluronic acid layer is removed from the film by water or saline, the polylactic acid-based resin can be pasted on any surface. Particularly for surgery, the film can be pasted on organs or the like so that biotissues are prevented from adhering to each other. Further, the acetylated hyaluronic acid can suppress bacterial growth better in comparison with other general-purpose water-soluble resin.

The invention claimed is:

1. A laminated film comprising one or more layers of acetylated hyaluronic acid layer having a thickness of 1 μm

TABLE 1

| | | Example 1 | Example 2 | Example 3 | Example 4 | Example 5 | Example 6 | Example 7 | Example 8 |
|---|---|---|---|---|---|---|---|---|---|
| Thickness | Acetylated hyaluronic acid layer [μm] | 50 | 1 | 100 | 50 | 50 | 50 | 50 | 50 |
| | Polylactic acid-based resin layer [nm] | 100 | 100 | 100 | 10 | 500 | 100 | 100 | 100 |
| Resin | Acetylated hyaluronic acid layer | AcHA-1 | AcHA-1 | AcHA-1 | AcHA-1 | AcHA-1 | AcHA-2 | AcHA-3 | AcHA-4 |
| | Weight average molecular weight [$\times 10^4$] | 99 | 99 | 99 | 99 | 99 | 135 | 230 | 128 |
| | Acetylation degree | 0.6 | 0.6 | 0.6 | 0.6 | 0.6 | 0.4 | 0.2 | 0.9 |
| Characteristics | Solubility | A | A | A | A | A | B | B | B |
| | Ability to induce microorganism development | A | A | A | A | A | A | A | A |
| | Mouse survival rate | A | A | A | A | A | A | A | A |
| | Pasting ability | A | A | A | A | A | A | A | A |

TABLE 2

| | | Comparative Example 1 | Comparative Example 2 | Comparative Example 3 | Comparative Example 4 |
|---|---|---|---|---|---|
| Thickness | Acetylated hyaluronic acid layer [μm] | 0.1 | 250 | 100 | 50 |
| | Polylactic acid-based resin layer [nm] | 100 | 100 | 5 | 5,000 |
| Resin | Acetylated hyaluronic acid layer | AcHA-1 | AcHA-1 | AcHA-1 | AcHA-1 |
| | Weight average molecular weight [$\times 10^4$] | 99 | 99 | 99 | 99 |
| | Acetylation degree | 0.6 | 0.6 | 0.6 | 0.6 |
| Characteristics | Solubility | C | B | C | A |
| | Ability to induce microorganism development | A | A | A | A |
| | Mouse survival rate | A | A | A | B |
| | Pasting ability | A | B | A | B | or more and 100 μm or less, provided on a side of a polylactic acid-based resin layer having a thickness of 10 nm or more and 500 nm or less.

2. The laminated film according to claim 1, wherein the acetylated hyaluronic acid has an acetylation degree of 0.1 or more and 0.9 or less.

3. The laminated film according to claim 2, wherein the acetylated hyaluronic acid has a weight average molecular weight of 100,000 or more and 3,000,000 or less in terms of hyaluronic acid.

4. The laminated film according to claim 1, wherein the acetylated hyaluronic acid has a weight average molecular weight of 100,000 or more and 3,000,000 or less in terms of hyaluronic acid.

5. A medical sheet comprising the laminated film according to claim 1.

6. A medical sheet comprising the laminated film according to claim 2.

7. A medical sheet comprising the laminated film according to claim 4.

* * * * *